United States Patent
Millet

(10) Patent No.: US 10,596,128 B2
(45) Date of Patent: *Mar. 24, 2020

(54) NON-RACEMIC BETA-HYDROXYBUTYRATE COMPOUNDS AND COMPOSITIONS ENRICHED WITH THE S-ENANTIOMER AND METHODS OF USE

(71) Applicant: AXCESS GLOBAL SCIENCES, LLC, Salt Lake City, UT (US)

(72) Inventor: Gary Millet, Salt Lake City, UT (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/224,485

(22) Filed: Dec. 18, 2018

(65) Prior Publication Data

US 2019/0183820 A1 Jun. 20, 2019

Related U.S. Application Data

(62) Division of application No. 15/936,849, filed on Mar. 27, 2018, now Pat. No. 10,245,243.

(60) Provisional application No. 62/607,578, filed on Dec. 19, 2017.

(51) Int. Cl.
| | | |
|---|---|---|
| *A61K 31/19* | (2006.01) | |
| *A61K 9/14* | (2006.01) | |
| *A23L 33/12* | (2016.01) | |
| *A61K 9/20* | (2006.01) | |
| *A61K 9/48* | (2006.01) | |
| *A23L 29/00* | (2016.01) | |
| *A61P 3/08* | (2006.01) | |
| *A61K 47/14* | (2017.01) | |
| *A23L 33/00* | (2016.01) | |
| *A23L 33/10* | (2016.01) | |
| *A23L 33/155* | (2016.01) | |

(52) U.S. Cl.
CPC .......... *A61K 31/19* (2013.01); *A23L 29/035* (2016.08); *A23L 33/10* (2016.08); *A23L 33/12* (2016.08); *A23L 33/30* (2016.08); *A61K 9/14* (2013.01); *A61K 9/20* (2013.01); *A61K 9/48* (2013.01); *A61K 47/14* (2013.01); *A61P 3/08* (2018.01); *A23L 33/155* (2016.08); *A23V 2002/00* (2013.01); *A23V 2250/182* (2013.01); *A23V 2250/192* (2013.01); *A23V 2250/1946* (2013.01); *A23V 2250/7106* (2013.01)

(58) Field of Classification Search
None
See application file for complete search history.

(56) References Cited

U.S. PATENT DOCUMENTS

| | | |
|---|---|---|
| 2,238,149 A | 4/1941 | Aeckerle |
| 5,093,044 A | 3/1992 | Wretlind |
| 5,116,868 A | 5/1992 | Chen et al. |
| 5,700,670 A | 12/1997 | Yamagishi et al. |
| 6,207,856 B1 | 3/2001 | Veech |
| 6,316,038 B1 | 11/2001 | Veech |
| 6,323,237 B1 | 11/2001 | Veech |
| 6,613,356 B1 | 9/2003 | Vlahakos |
| 7,351,736 B2 | 4/2008 | Veech |
| 8,101,653 B2 | 1/2012 | Veech |
| 8,124,589 B2 | 2/2012 | Henderson |
| 8,426,468 B2 | 4/2013 | Henderson |
| 8,642,654 B2 | 2/2014 | Clarke et al. |
| 9,138,420 B2 | 9/2015 | D'Agostino et al. |
| 9,211,275 B2 | 12/2015 | Clarke et al. |
| 9,675,577 B2 | 6/2017 | D'Agostino et al. |
| 9,795,580 B2 | 10/2017 | Weeber et al. |
| 9,957,246 B2 | 5/2018 | Stinchcomb et al. |
| 2001/0041736 A1 | 11/2001 | Veech |
| 2005/0129783 A1 | 6/2005 | McCleary |
| 2008/0287372 A1 | 11/2008 | Henderson |
| 2009/0253781 A1 | 10/2009 | Veech |
| 2010/0041751 A1 | 2/2010 | Henderson |
| 2010/0197758 A1 | 8/2010 | Andrews et al. |
| 2010/0298294 A1 | 11/2010 | Clarke |
| 2012/0071548 A1 | 3/2012 | Veech |
| 2013/0079406 A1 | 3/2013 | Veech |
| 2016/0256411 A1 | 9/2016 | Aung-Din |
| 2017/0258745 A1 | 9/2017 | Millet |
| 2017/0296501 A1* | 10/2017 | Lowery ............... A61K 45/06 |
| 2017/0298339 A1 | 10/2017 | Hanson et al. |
| 2017/0304564 A1 | 10/2017 | DeHaan et al. |
| 2019/0313682 A1 | 10/2019 | Nagel |

FOREIGN PATENT DOCUMENTS

| | | |
|---|---|---|
| CN | 1347319 | 5/2002 |
| EP | 2283834 | 2/2011 |

(Continued)

OTHER PUBLICATIONS

International Search Report in PCT/US18/62093 dated Feb. 1, 2019.

(Continued)

*Primary Examiner* — Dennis Heyer
(74) *Attorney, Agent, or Firm* — Workman Nydegger

(57) ABSTRACT

Ketogenic compositions including a non-racemic mixture of beta-hydroxybutyrate (BHB) enriched with the S-enantiomer are formulated to control ketone body levels in a subject. The non-racemic mixture of BHB is enriched with the S-enantiomer to modulate the effect of ketone bodies in the subject and control the rate at which ketosis is achieved. In some aspects a composition for controlling ketone body level in a subject contains a dietetically or pharmaceutically acceptable carrier and a non-racemic mixture of S-beta-hydroxybutyrate and R-beta-hydroxybutyrate, wherein the non-racemic mixture contains from about 52% to 99% by enantiomeric equivalents of S-beta-hydroxybutyrate enantiomer and from about 48% to about 1% by enantiomeric equivalents of R-beta-hydroxybutyrate enantiomer.

20 Claims, No Drawings

(56) References Cited

FOREIGN PATENT DOCUMENTS

| JP | 11060434 | 3/1999 |
|---|---|---|
| JP | 2002521330 | 7/2002 |
| RU | 2345546 | 4/2008 |
| WO | WO8703808 | 7/1987 |
| WO | WO 98/41200 | 9/1998 |
| WO | WO 03/070823 | 8/2003 |
| WO | WO2005107724 | 11/2005 |
| WO | WO2007115282 | 10/2007 |
| WO | WO2008005818 | 1/2008 |
| WO | WO 2008/021394 | 2/2008 |
| WO | WO 2008/024408 | 2/2008 |
| WO | WO2011101171 | 8/2011 |
| WO | WO 2014153416 | 9/2014 |
| WO | WO2016123229 | 8/2016 |
| WO | WO 2017/208217 | 12/2017 |
| WO | WO 2018/089863 | 5/2018 |

OTHER PUBLICATIONS

International Search Report in PCT/US18/62096 dated Feb. 11, 2019.
Haywood A, Glass BD. Pharmaceutical excipients—where do we begin? Australian Prescriber. 2011; 34: 112-114.
Dolson, Laura. How to Test Your Blood for Ketones. Downloaded Apr. 1, 2015. http://lowcarbdiets.about.com/od/KetogenicDiets/a/How-to-Test-Blood-For-Ketones.htm.
Nova Max Plus Glucose and Ketone Testing with One Monitor. Downloaded Apr. 1, 2015. http://www.novacares.com/nova-max-plus/.
Serum Ketones Test. MedlinePlus Medical Encyclopedia. Downloaded Apr. 1, 2015. http://www.nlm.nih.gov/medlineplus/ency/article/003498.htm.
It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.
A New Toy Measuring Blood Ketones. Diet Doctor, Aug. 21, 2012. Dowloaded Apr. 1, 2015. http://www.dietdoctor.com/a-new-toy-measuring-blood-ketoones.
Precision Xtra vs. NovaMax Plus: Ketone Meter Evaluation. Jimmy Moore's Livin' La Vida Low Carb Blog. Downloaded Apr. 1, 2015. http://livinlavidalowcarb.com/blog/precision-xtra-vs-novamax-plus-ketone-meter-evaluation/15918.
Kirsch, Jr et al. "Butanediol Induced Ketosis Increases Tolerance to Hypoxia in the Mouse." Stroke. 1980, vol. 11, No. 5, pp. 506-513.
Kossoff, Eric H. et al. "Optimal Clinical Management of Children Receiving the Ketogenic Diet: Recommendations of the International Ketogenic Diet Study Group." Epilepsia, Feb. 2009;50(2):304-17. Epub Sep. 23, 2008.
Henderson, Samuel T. "Ketone Bodies as a Therapeutic for Alzheimer's Disease." Neurotherapeutics. Jul. 2008;5 3 3):470-80.
Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essent Fatty Acids. Mar. 2004;70(3):309-19.
Krotkiewski, M. "Value of VLCD Supplementation with Medium Chain Triglycerides." I'nt J Obes Relat Metab Disord. Sep. 2001;25(9):1 393/\00.
PCT International Search Report and Written Opinion issued by the International Searching Authority dated Jul. 15, 2014 or International Patent Application No. PCT/US2014/031237.

Bastin et al., "Salt Slection and Optimisation Procedures for Pharmaceutical New Chemical Entities", American Chemical Society and The Royal Society of Chemistry, vol. 4, No. 5, 2000, pp. 427-435.
Arnold, Instant Ketosis?, (2013), Aug. 4, 2013 (retrieved on Apr. 21, 2017), p. 1-3. Retrieved from the internet; URL: < http://patrickarnoldblog.com/instant-ketosis/. (Year: 2013).
Parker, Steve, "Ketogenic Mediterranean Diet: Version 2.3," Nov. 23, 2010, pp. 1-3. (Year: 2010).
Sajewicz et al. in Journal of Liquid Chromatography & Related Technologies, 33:1047-1057 (2010) (Year: 2010).
Shigeno etal. in Biosci. Biotech. Biochem., 56(2), 320-323 (1992) (Year: 1992).
Optical Purity and Enantiomeric Excess at https://www.masterorganicchemistry.com/2017/02/24/optical-purity-and-enantiomeric-excess/. (Retrieved from the Internet Nov. 6, 2018) (Year: 2018).
Tisdale, "Reduction of weight loss and tumour size in a cachexia model by a high fat diet", British Journal of Cancer, Jul. 1987, vol. 56, p. 39-43.
U.S. Appl. No. 14/455,385, dated Jan. 2, 2015, Office Action.
U.S. Appl. No. 14/860,092, dated Mar. 9, 2016, Office Action.
U.S. Appl. No. 14/860,092, dated Oct. 17, 2016, Office Action.
U.S. Appl. No. 15/610,668, dated Jul. 25, 2018, Office Action.
U.S. Appl. No. 15/454,157, dated Jan. 11, 2018, Office Action.
U.S. Appl. No. 15/454,157, dated Jun. 13, 2018, Office Action.
U.S. Appl. No. 15/936,820, dated Nov. 14, 2018, Office Action.
U.S. Appl. No. 15/936,849, dated Nov. 14, 2018, Office Action.
U.S. Appl. No. 15/454,157, dated Feb. 26, 2019, Notice of Allowance.
U.S. Appl. No. 15/936,849, dated Jan. 24, 2019, Notice of Allowance.
Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.
International Search Report in PCT/US19/27214 dated Jun. 25, 2019.
Written Opinion in PCT/US19/27214 dated Jun. 25, 2019.
U.S. Appl. No. 16/272,328, dated Jul. 29, 2019, Office Action.
Pubchem, "Acetoacetic acid" Electronic Resource: https://pubchem.ncbi.nlm.nih.gov/compound/Acetoacetic-acid, Retrieved on Sep. 3, 2019.
Arendash et al. "Caffeine and Coffee as Therapeutics Against Alzheimer's Disease", Journal of Alzheimer's Disease 20, 2010, S117-S126.
Kesl, et al., "Effects of exogenous ketone supplementation on blood ketone, glucose, triglyceride, and lipoprotein levels in Sprague-Dawley rats", Nutrition & Metabolism (2016).
Extended European Search Report issued in PCT/US2017021886 dated Oct. 17, 2019.
International Search Report and Written Opinion issued in PCT/US19/48364 dated Nov. 15, 2019.
International Search Report and Written Opinion issued in PCT/US19/48357 dated Nov. 18, 2019.
U.S. Appl. No. 16/272,359, filed Feb. 11, 2019, Notice of Allowance.
U.S. Appl. No. 16/381,202, filed Oct. 22, 2019, Office Action.
U.S. Appl. No. 16/224,485, filed Nov. 27, 2019, Notice of Allowance.
U.S. Appl. No. 16/224,408, filed Nov. 27, 2019, Notice of Allowance.

* cited by examiner

NON-RACEMIC BETA-HYDROXYBUTYRATE COMPOUNDS AND COMPOSITIONS ENRICHED WITH THE S-ENANTIOMER AND METHODS OF USE

CROSS-REFERENCE TO RELATED APPLICATIONS

This Application is a division of U.S. patent application Ser. No. 15/936,849, filed Mar. 27, 2018, which claims the benefit of U.S. Provisional Patent Application No. 62/607,578, filed Dec. 19, 2017, the disclosures of which are incorporated herein by reference in their entirety.

BACKGROUND

1. Field of the Invention

Disclosed herein are non-racemic beta-hydroxybutyrate compounds, salts, esters, and compositions enriched with the S-enantiomer of beta-hydroxybutyrate and methods for controlling and/or modulating blood levels and/or the effects of ketone bodies in a subject.

2. Related Technology

In periods of fasting, extreme exercise, and/or low carbohydrate consumption, glucose and glycogen stores in the body are rapidly used and can become quickly depleted. Failure to replenish glucose stores as they become depleted causes the body to metabolically shift to the creation and use of ketone bodies for energy ("ketosis"). Ketone bodies can be used by cells of the body as a fuel to satisfy the body's energy needs, including the brain and heart. During prolonged fasting, for example, blood ketone levels can increase to 2-3 mmol/L or more. It is conventionally understood that when blood ketones rise above 0.5 mmol/L, the heart, brain and peripheral tissues are using ketone bodies (e.g., beta-hydroxybutyrate and acetoacetate) as the primary fuel source. This condition is referred to as ketosis. Between 1.0 mmol/L and 3.0 mmol/L the condition is called "nutritional ketosis."

Upon transitioning into ketosis, or in other words, during ketogenic metabolism in the liver, the body uses dietary and bodily fats as a primary energy source. Consequently, once in ketosis, one can induce loss of body fat by controlling dietary fat intake and maintaining low carbohydrate intake and blood level to sustain ketosis.

While in ketosis, the body is in ketogenisis and essentially burning fat for its primary fuel. The body cleaves fats into fatty acids and glycerol and transforms fatty acids into acetyl CoA molecules, which are then eventually transformed through ketogenesis into the water soluble ketone bodies beta-hydroxybutyrate ("β-hydroxybutyrate" or "BHB"), acetoacetate (also known as acetylacetonate), and acetone in the liver. Beta-hydroxybutyrate and acetoacetate are the ketone bodies used by the body for energy while acetone is removed and expelled as a by-product of ketogenesis.

The metabolism of ketone bodies is associated with several beneficial effects, including anticonvulsant effects, enhanced brain metabolism, neuroprotection, muscle sparing properties, and improved cognitive and physical performance. Science-based improvements in efficiency of cellular metabolism, managed through ketone supplementation, can have beneficial impacts on physical, cognitive health, and psychological health, and a long-term impact on health with respect to common avoidable diseases such as obesity, cardiovascular disease, neurodegenerative diseases, diabetes, and cancer.

Despite the many health advantages of pursuing a ketogenic diet or lifestyle and maintaining a state of nutritional ketosis, there remain significant barriers to pursuing and maintaining a ketogenic state. One of these barriers is the difficulty of transitioning into a ketogenic state. The fastest endogenous way to entering ketosis through depleting glucose stores in the body is by fasting combined with exercise. This is physically and emotionally demanding and is extremely challenging even for the most motivated and disciplined.

Additionally, the transition into ketosis is often accompanied by hypoglycemia, which can cause lethargy and light-headedness in many, resulting in an uncomfortable physiological and mental state commonly referred to as the "low-carb flu." In addition, many people experience a down regulation in their metabolism as the body naturally goes into an "energy-saving" mode. Some suggest that these transitory symptoms may last as long as two to three weeks. During this transition period, if a subject consumes a meal or snack containing carbohydrates above the restrictive amount, there is an immediate termination of ketogenisis, exiting the body from its state of ketosis, as the body shifts back to glucose utilization for its primary fuel and the transition into ketosis must begin anew.

If a subject is successful in establishing ketosis, the act of sustaining ketosis is likewise difficult, if not more difficult, due to the need to maintain a rigid dietary ratio of carbohydrates and protein to fats. It is further complicated by the disruption of normal electrolyte balances that often occurs when transitioning into and maintaining a ketogenic state. The depletion and lowering of glycogen stores in the liver and muscles lessens the ability of the body to retain water, leading to more frequent urination, and accordingly, a greater loss of electrolytes. Further, the drop in insulin levels caused by ketosis effects the rate at which certain electrolytes are extracted by the kidneys, additionally lowering electrolyte levels in the body. Negative effects of electrolyte imbalance include muscle aches, spasms, twitches and weakness, restlessness, anxiety, frequent headaches, feeling very thirsty, insomnia, fever, heart palpitations or irregular heartbeats, digestive issues such as cramps, constipation or diarrhea, confusion and trouble concentrating, bone disorders, joint pain, blood pressure changes, changes in appetite or body weight, fatigue (including chronic fatigue syndrome), numbness in joints, and dizziness, especially when standing up suddenly.

Some compositions used to promote ketosis in a mammal include a racemic mixture of beta-hydroxybutyrate (RS-beta-hydroxybutyrate or DL-beta-hydroxybutyrate). Other compositions, such as those disclosed in U.S. Patent Publication No. 2017/0296501 to Lowery et al., contain only the endogenous form of beta-hydroxybutyrate, or R-beta-hydroxybutyrate, and none of the non-endogenous enantiomer, or S-beta-hydroxybutyrate. Others, such as those disclosed in U.S. Pat. No. 8,642,654 to Clarke et al., consist mostly or entirely of a single beta-hydroxybutyrate ester (3R)-hydroxybutyl (3R)-hydroxybutyrate. Other enantiomers, such as (3R)-hydroxybutyl (3 S)-hydroxybutyrate, (3 S)-hydroxybutyl (3R)-hydroxybutyrate, and (3 S)-hydroxybutyl (3 S)-hydroxybutyrate, are mostly or entirely omitted. The omission of enantiomers that are not the endogenous form of beta-hydroxybutyrate is based on the view that S-beta-hydroxybutyrate (aka (3 S)-hydroxybutyrate) is ineffective or even harmful.

BRIEF SUMMARY

Disclosed herein are compositions and methods for controlling ketone body levels in a subject, including promoting and/or sustaining ketosis in a subject over an extended period of time. Example compositions include a non-racemic mixture of S-beta-hydroxybutyrate and R-beta-hydroxybutyrate, wherein the non-racemic mixture contains from 52% to 99% by enantiomeric equivalents of the S-beta-hydroxybutyrate enantiomer and 48% to 1% by enantiomeric equivalents of the R-beta-hydroxybutyrate enantiomer.

The non-racemic mixture of S-beta-hydroxybutyrate and R-beta-hydroxybutyrate contains more of the S-beta-hydroxybutyrate enantiomer than the endogenous form (R-enantiomer) produced by a mammal in order to provide a more controlled and sustained ketogenic effect compared to a racemic mixture and/or compositions enriched with the R-enantiomer. Because the R-beta-hydroxybutyrate enantiomer is endogenously produced by a mammal during ketosis, administering the R-beta-hydroxybutyrate enantiomer to a subject provides a quantity that can be immediately utilized by the body, such as for producing energy (e.g., as an alternative energy source to glucose). However, this effect is modulated and extended when the S-enantiomer is the predominant component.

Contrary to compositions that are deliberately enriched with the R-enantiomer or that minimize or eliminate S-beta-hydroxybutyrate altogether, the non-racemic mixture is enriched with the S-beta-hydroxybutyrate enantiomer, which is not endogenously produced by a mammal, in order to produce one or more desired effects in the mammal, as discussed herein.

In some embodiments, the compositions disclosed herein can be used in a method for increasing ketone body level in a subject, including promoting and/or sustaining ketosis in a subject, comprising administering to a subject in need thereof a nutritionally or pharmaceutically effective amount of one or more compositions disclosed herein. Examples of beneficial effects of increased ketone body level in a subject include one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, or improved body composition.

In some embodiments, administering the non-racemic mixture of S-beta-hydroxybutyrate and R-beta-hydroxybutyrate in the enantiomeric ratios or percentages disclosed herein provide one or more of: increased endogenous production of R-beta-hydroxybutyrate and acetoacetate; endogenous conversion of the S-beta-hydroxybutyrate into one or both of R-beta-hydroxybutyrate and acetoacetate; endogenous conversion of the S-beta-hydroxybutyrate into fatty acids and sterols; prolonged ketosis; metabolism of the S-beta-hydroxybutyrate independent of conversion to R-beta-hydroxybutyrate and/or acetoacetate; increased fetal development; increased growth years; reduced endogenous production of acetone during ketosis; signaling by the S-beta-hydroxybutyrate that modulates metabolism of R-beta-hydroxybutyrate and glucose; antioxidant activity; and production of acetyl-CoA.

In some embodiments, the composition may include a carrier and up to 100% of S-beta-hydroxybutyrate enantiomer and no R-beta-hydroxybutyrate enantiomer.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

DETAILED DESCRIPTION

I. Definitions

As used herein "beta-hydroxybutyrate," also known as β-hydroxybutyrate, βHB or BHB, means a compound having the general formula $CH_3CH_2OHCH_2COOH$ and the following chemical structure:

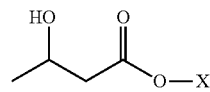

where,

X can be hydrogen, metal ion, amino cation, such as from an amino acid, alkanyl, alkenyl, or aryl.

Whether beta-hydroxybutyrate is the S- or R-enantiomer depends on the tetrahedral orientation of the hydroxy (or oxy group in the case of an ester) on the 3-carbon (beta-carbon) in relationship to the planar carboxyl group.

Beta-hydroxybutyrate, typically R-beta-hydroxybutyrate, which is the endogenous form, can be utilized by a patient's body as a fuel source during instances of low glucose levels in the subject or when a patient's body is supplemented with a usable form of beta-hydroxybutyrate. Beta-hydroxybutyrate is commonly referred to as a "ketone body."

As used herein, a "ketogenic composition" is formulated to increase ketone body level in a subject, including inducing and/or sustaining a state of elevated ketone bodies at a desired level, such as ketosis, in a subject to which it is administered.

As used herein, "subject" or "patient" refers to members of the animal kingdom, including mammals, such as but not limited to, humans and other primates; rodents, fish, reptiles, and birds. The subject may be any animal requiring therapy, treatment, or prophylaxis, or any animal suspected of requiring therapy, treatment, or prophylaxis. Prophylaxis means that regiment is undertaken to prevent a possible occurrence, such as where a high glucose or diabetes is identified. "Patient" and "subject" are used interchangeably herein.

"Ketosis" as used herein refers to a subject having blood ketone levels within the range of about 0.5 mmol/L and about 16 mmol/L in a subject. Ketosis may improve mitochondrial function, decrease reactive oxygen species production, reduce inflammation and increase the activity of neurotrophic factors. "Keto-adaptation" as used herein refers to prolonged nutritional ketosis (>1 week) to achieve a sustained nonpathological "mild ketosis" or "therapeutic ketosis."

In some cases, "elevated ketone body level" may not mean that a subject is in a state of "clinical ketosis" but nevertheless has an elevated supply of ketones for producing energy and/or for carrying out other beneficial effects of ketone bodies. For example, a subject that is "ketone adapted" may not necessarily have elevated blood serum levels of ketone bodies but rather is able to utilize available ketone bodies more rapidly compared to a subject that is not "ketone adapted." In such case, "elevated ketone body level" can refer to the total quantity and/or rate of ketone bodies being utilized by the subject rather than blood plasma levels per se.

The term "medium chain triglycerides" (MCT) refers to molecules having a glycerol backbone attached to three medium chain fatty acids. Medium chain fatty acids can range from 6 to 12 carbon atoms in length, and more likely 8 to 10 carbon atoms in length. Exemplary fatty acids are caprylic acid, also known as octanoic acid, comprising 8 carbon molecules, and capric acid, also known as decanoic acid, comprising 10 carbon molecules. MCTs, medium chain fatty acids, and mono- and di-glycerides are ketone body precursors that can provide an additional source for the production of ketone bodies independent of beta-hydroxybutyrate.

The term "administration" or "administering" is used herein to describe the process in which the disclosed compositions are delivered to a subject. The composition may be administered in various ways including oral, intragastric, and parenteral (referring to intravenous and intra-arterial and other appropriate parenteral routes), among others.

II. Non-Racemic Beta-Hydroxybutyrate Compositions

Compositions for increasing ketone body level in a subject, including controlling and/or modulating ketosis, comprise a non-racemic mixture of S-beta-hydroxybutyrate and R-beta-hydroxybutyrate, wherein the non-racemic mixture contains from 52% to 99% by enantiomeric equivalents of the S-beta-hydroxybutyrate enantiomer and 48% to 1% by enantiomeric equivalents of the R-beta-hydroxybutyrate enantiomer.

In some embodiments, the non-racemic mixture of R-beta-hydroxybutyrate and S-beta-hydroxybutyrate contains from 53% to 98%, 55% to 96%, 57% to 93%, 60% to 90%, or 65% to 85% by enantiomeric equivalents of the S-beta-hydroxybutyrate enantiomer and 47% to 2%, 45% to 4%, 3% to 7%, 40% to 10%, or 35% to 15%, by enantiomeric equivalents of the R-beta-hydroxybutyrate enantiomer.

The non-racemic mixture of S-beta-hydroxybutyrate and R-beta-hydroxybutyrate contains more of the S-beta-hydroxybutyrate enantiomer rather than the endogenous form produced by a mammal, which is the R-beta-hydroxybutyrate enantiomer, in order to provide for more controlled, gradual, extended, and/or modulated ketogenic effect compared to either a racemic mixture or composition enriched with the R-beta-hydroxybutyrate enantiomer. Because the R-beta-hydroxybutyrate enantiomer is endogenously produced by a mammal during ketosis, administering the R-beta-hydroxybutyrate enantiomer to a subject provides an additional quantity and/or increased blood plasma level that can be immediately utilized by the body, such as for producing energy (e.g., as an alternative energy source to glucose). However, this effect is modulated and extended due to the S-enantiomer being the predominant component.

Contrary to compositions that deliberately minimize or eliminate S-beta-hydroxybutyrate, the non-racemic mixture contains a majority quantity of the S-beta-hydroxybutyrate enantiomer, which is not endogenously produced by a mammal, in order to produce one or more desired effects in the mammal. For example, administering S-beta-hydroxybutyrate along with R-beta-hydroxybutyrate can result in at least one of: (1) increased endogenous production of R-beta-hydroxybutyrate and acetoacetate; (2) endogenous conversion of the S-beta-hydroxybutyrate into one or both of R-beta-hydroxybutyrate and acetoacetate; (3) endogenous conversion of the S-beta-hydroxybutyrate into fatty acids and sterols; (4) prolonged ketosis; (5) metabolism of the S-beta-hydroxybutyrate independent of conversion to R-beta-hydroxybutyrate and/or acetoacetate; (6) increased fetal development; (7) increased growth years; (8) reduced endogenous production of acetone during ketosis; (9) signaling by the S-beta-hydroxybutyrate that modulates metabolism of R-beta-hydroxybutyrate and glucose; (10) antioxidant activity; and (11) production of acetyl-CoA.

The non-racemic mixture of S-beta-hydroxybutyrate and R-beta-hydroxybutyrate can be used, for example, to produce one or more desired effects in the subject, including but not limited to, appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, or improved body composition.

In some embodiments, the composition may include a carrier and up to 100% of S-beta-hydroxybutyrate enantiomer and no R-beta-hydroxybutyrate enantiomer.

The S-beta-hydroxybutyrate and R-beta-hydroxybutyrate can be provided in various forms, such as salts and esters. The percent of enantiomer equivalents of each of the S-beta-hydroxybutyrate and R-beta-hydroxybutyrate is defined by the molar quantity of either S-beta-hydroxybutyrate or R-beta-hydroxybutyrate divided by the total molar quantity of both S-beta-hydroxybutyrate and R-beta-hydroxybutyrate. The amounts of any cations forming salts and/or alcohols forming esters are excluded and do not count in determining the percent of enantiomeric equivalents of each of S-beta-hydroxybutyrate and R-beta-hydroxybutyrate.

In some embodiments, the non-racemic mixture of R-beta-hydroxybutyrate and S-beta-hydroxybutyrate is provided in a composition that includes a dietetically or pharmaceutically acceptable carrier. Examples include powders, liquids, tablets, capsules, food products, food additives, beverages, beverage additives, candies, suckers, pastilles, food supplements, sprays, injectables, and suppositories.

In some embodiments, the non-racemic mixture of S-beta-hydroxybutyrate and R-beta-hydroxybutyrate can be provided as a salt, such as one or more salts of alkali metals, alkaline earth metals, transition metals, amino acids, or metabolites of amino acids. Examples include lithium salts, sodium salts, potassium salts, magnesium salts, calcium salts, zinc salts, iron salts (as iron II and/or iron III), chromium salts, manganese salts, cobalt salts, copper salts, molybdenum salts, selenium salts, arginine salts, lysine salts, leucine salts, isoleucine salts, histidine salts, ornithine salts, citrulline salts, glutamine salts, and creatine salts.

In some embodiments, the non-racemic mixture of S-beta-hydroxybutyrate and R-beta-hydroxybutyrate can be provided as one or more esters, such as mono-, di-, tri-, oligo-, and polyesters. Examples include mono-ester of ethanol, mono-ester of 1-propanol, mono-ester of 1,2-propanediol, di-ester of 1,2-propanediol, mono-ester of 1,3-propanediol, di-ester of 1,3-propanediol, mono-ester of S—, R—, or S—R-1,3-butanediol, di-ester of S—, R—, or S—R-

1,3-butanediol, mono-ester of glycerin, (3 S)-hydroxybutyl (3 S)-hydroxybutyrate mono-ester, (3R)-hydroxybutyl (3 S)-hydroxybutyrate, mono-ester, di-ester of glycerin, tri-ester of glycerin, ester of acetoacetate, dimers, trimers, oligomers, and polyesters containing repeating units of beta-hydroxybutyrate, and complex oligomers or polymers of beta-hydroxybutyrate and one or more other hydroxy-carboxylic acids, such as lactic acid, citric acid, acetoacetic acid, quinic acid, shikimic acid, salicylic acid, tartaric acid, and malic acid, and/or beta-hydroxybutyrate and or one or more diols, such as 1,3-propanediol and 1,3-butanediol, and one or more polyacids, such as tartaric acid, citric acid, malic acid, succinic acid, and fumaric acid. While (3R)-hydroxybutyl (3R)-hydroxybutyrate mono-ester can be included, it should not cause the amount of R-hydroxybutyrate to exceed 48% by enantiomeric equivalents.

In some embodiments, the composition may further include at least one medium chain fatty acid, or a mono-, di- or triglyceride of the at least one medium chain fatty acid, wherein the medium chain fatty acid has from 6 to 12 carbons, preferably from 8 to 10 carbons. Although less preferred, the composition may comprise at least one short chain fatty acid, or a mono-, di- or triglyceride of the at least one short chain fatty acid, having less than 6 carbons and/or at least one long chain fatty acid, or a mono-, di- or triglyceride of the at least one long chain fatty acid, having more than 12 carbons.

Examples and sources of the medium chain fatty acid, or an ester thereof such as a medium chain triglyceride, include coconut oil, coconut milk powder, fractionated coconut oil, palm oil, palm kernel oil, caprylic acid, capric acid, isolated medium chain fatty acids, such as isolated hexanoic acid, isolated octanoic acid, isolated decanoic acid, medium chain triglycerides either purified or in natural form such as coconut oil, and ester derivatives of the medium chain fatty acids ethoxylated triglyceride, enone triglyceride derivatives, aldehyde triglyceride derivatives, monoglyceride derivatives, diglyceride derivatives, and triglyceride derivatives, and salts of the medium chain triglycerides. Ester derivatives optionally include alkyl ester derivatives, such as methyl, ethyl, propyl, butyl, hexyl, etc.

The administration of a non-racemic mixture of S-beta-hydroxybutyrate and R-beta-hydroxybutyrate results in controlled, prolonged, and modulated blood levels of ketone bodies, thereby exploiting the metabolic and physiological advantages of sustained ketosis. Raising the levels of ketone bodies in the blood provides a subject with greater flexibility in diet options as compared to methods that aim to induce and sustain ketosis based on diet alone (e.g., based on fasting and/or limited carbohydrate intake). For example, a subject that has been administered an appropriate amount of a non-racemic mixture of S-beta-hydroxybutyrate and R-beta-hydroxybutyrate will be able to eat an occasional carbohydrate or sugar-based food without jeopardizing the ketogenic state and shifting back into a glucose-based metabolic state. Further, such administration facilitates easier transitioning into a ketogenic state while reducing or eliminating the detrimental effects typically associated with entering ketosis.

In some embodiments, a ketogenic composition additionally includes a therapeutically effective amount of vitamin $D_3$. Vitamin $D_3$ is believed to work in conjunction with magnesium and calcium to promote good bone health and to prevent undesirable calcification of soft tissues. In preferred embodiments, vitamin $D_3$ is included in an amount such that an average daily dose of the ketogenic composition includes about 200 IU ("International Units") to about 8000 IU, or about 400 IU to about 4000 IU, or about 600 IU to about 3000 IU of vitamin $D_3$. In some embodiments, vitamin $D_3$ is included in an amount such that an average daily dose of the ketogenic composition includes about 5 µg to about 200 µg, or about 10 µg to about 100 µg, or about 15 µg to about 75 µg of vitamin $D_3$.

Some embodiments also include one or more additional ketone precursors or supplements. These additional ketone precursors or supplements might include acetoacetate, ketone esters, and/or other compounds that cause a rise in blood ketone levels without adding more electrolytes to the bloodstream. Other additives include metabolites that enhance the effect or transport of ketone bodies into mitochondria, caffeine, theobromine, and nootropics, such as L-alpha glycerylphosphorylcholine ("alpha GPC").

The composition may include flavoring agents that help mask the otherwise poor taste of beta-hydroxybutyrate compounds. These include essential oils, such as peppermint, natural and artificial sweeteners, and other flavorants known in the art.

In some embodiments, ketogenic compositions may further includes one or more additional components configured to lower the hygroscopicity of the composition. For example, various anticaking agents, flow agents, and/or moisture absorbers, in types and amounts that are safe for consumption, may be included. Such additional components may include one or more of an aluminosilicate, ferrocyanide, carbonate or bicarbonate salt, silicate (e.g., sodium or calcium silicate), phosphate salt (e.g., tricalcium phosphate), talcum, powdered cellulose, and the like.

III. Administration

In some embodiments, the compositions disclosed herein can be used in a method for increasing ketone body level, including promoting and/or sustaining ketosis, in a subject comprising administering to a subject in need thereof a nutritionally or pharmaceutically effective amount of one or more compositions disclosed herein. Examples of beneficial effects of increasing ketone body level, including promoting and/or sustaining ketosis, in a subject include one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, or improved body composition.

In some embodiments, administering the non-racemic mixture of S-beta-hydroxybutyrate and R-beta-hydroxybutyrate in the enantiomeric ratios or percentages disclosed herein provide one or more of increased endogenous production of R-beta-hydroxybutyrate and acetoacetate; endogenous conversion of the S-beta-hydroxybutyrate into one or both of R-beta-hydroxybutyrate and acetoacetate; endogenous conversion of the S-beta-hydroxybutyrate into fatty acids and sterols; prolonged ketosis; metabolism of the S-beta-hydroxybutyrate independent of conversion to R-beta-hydroxybutyrate and/or acetoacetate; increased fetal development; increased growth years; reduced endogenous production of acetone during ketosis; signaling by the S-beta-hydroxybutyrate that modulates metabolism of R-beta-hydroxybutyrate and glucose; antioxidant activity; and production of acetyl-CoA.

Ketogenic compositions described herein may be administered to a subject in therapeutically effective dosages and/or in frequencies to induce or sustain ketosis. In some embodiments, a single dose will include an amount of non-racemic mixture of S-beta-hydroxybutyrate and R-beta-hydroxybutyrate ranging from about 0.5 gram to about 25 grams, or about 0.75 gram to about 20 grams, or about 1 gram to about 15 grams, or about 1.5 grams to about 12 grams.

In some embodiments, the ketogenic compositions can include or be administered together with other supplements, such as vitamin $D_3$, vitamins, minerals, and others known in the art.

In some embodiments, the compositions may further include one or more medium chain fatty acids, fatty acid esters, or mono-, di- or triglycerides of medium chain fatty acids in order to provide an additional source of ketone bodies, as discussed herein, for sustaining ketosis for a longer period of time compared to if just the non-racemic mixture of S-beta-hydroxybutyrate and R-beta-hydroxybutyrate is used by itself. In some embodiments, the composition is preferably administered such that the ratio of the non-racemic mixture of S-beta-hydroxybutyrate and R-beta-hydroxybutyrate to medium chain fatty acid (or ester thereof) ranges from about 4:1 to about 1:4, or from about 2:1 to about 1:2, or from about 1.5:1 to about 1:1.5. Short chain fatty acids, esters, and glycerides thereof, though less preferred, can be used in addition to or instead of medium chain fatty acids, fatty acid esters, or glycerides thereof.

In some embodiments, the subject preferably follows a ketogenic diet that restricts intake of carbohydrates and protein during the period of administration of the composition. In one example embodiment, the subject may restrict the dietary intake to a ratio of about 65% fat, about 25% protein, and about 10% carbohydrates. The resulting therapeutic ketosis provides a rapid and sustained keto-adaptation as a metabolic therapy for a wide range of metabolic disorders, and provides nutritional support for therapeutic fasting, weight loss, and performance enhancement. As such, the composition is typically administered once per day, twice per day, or three times per day to a subject desiring to promote and/or sustain a state of ketosis.

In a preferred embodiment, ketogenic compositions can be administered via oral administration in solid and/or powdered form, such as in a powdered mixture (e.g., powder filled gelatin capsules), hard-pressed tablets, or other oral administration route known to those skilled in the art.

In some embodiments, multiple doses of the composition are administered over a period of time. The frequency of administration of the composition can vary depending on any of a variety of factors, such as timing of treatment from previous treatments, objectives of the treatment, and the like. The duration of administration of the composition (e.g., the period of time over which the agent is administered), can vary depending on any of a variety of factors, including subject response, desired effect of treatment, etc.

The amount of the composition to be administered can vary according to factors such as the degree of susceptibility of the individual, the age, sex, and weight of the individual, idiosyncratic responses of the individual, and the like. The "therapeutically effective amount" is that amount necessary to promote a therapeutically effective result in vivo (i.e., therapeutic ketosis). In accordance with the present disclosure, a suitable single dose size is a dose that is capable of preventing or alleviating (reducing or eliminating) a symptom in a patient when administered one or more times over a suitable time period.

The amount of composition administered will depend on potency, absorption, distribution, metabolism, and excretion rates of unused ketone bodies, electrolytes, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The compounds may be administered once, or may be divided and administered over intervals of time. It is to be understood that administration may be adjusted according to individual need and professional judgment of a person administrating or supervising the administration of the compositions.

IV. Examples

The following is a description of exemplary non-racemic mixtures of S-beta-hydroxybutyrate and R-beta-hydroxybutyrate compositions and other ketogenic compositions useful for raising ketone levels in a subject, including inducing and/or modulating a ketogenic state in a subject to which they are administered. It should be appreciated that the beta-hydroxybutyrate compounds described in the examples can be in the form of salts, esters, dimers, trimers, oligomers, and polymers, as discussed herein. The important thing from the standpoint of the examples is the enantiomeric percentages or ratios of S-beta-hydroxybutyrate and R-beta-hydroxybutyrate. In some cases, the compositions can be a blend of salts and esters to provide a desired electrolyte balance and/or modulation of ketosis. The compositions can also be combined with medium chain fatty acids, esters, glycerides, and other supplements as disclosed herein to provide a desired level of elevated ketone bodies and other effects.

Example 1

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 52% by enantiomeric equivalents of the S-beta-hydroxybutyrate enantiomer and 48% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture. On the other hand, including the S-beta-hydroxybutyrate enantiomer provides for a longer state of ketosis and/or other benefits as disclosed herein.

The non-racemic mixture is readily administered as a ketogenic composition, such as in powder form as a dietary supplement mixed with food or drink, in the form of one or more capsules or tablets, or in liquid form such as a mouth spray.

Example 2

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 53% by enantiomeric equivalents of the S-beta-hydroxybutyrate enantiomer and 47% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixture of Example 1. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 3

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 55% by enantiomeric equivalents of the S-beta-hydroxybutyrate enantiomer and 45% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1 and 2. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 4

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 57% by enantiomeric equivalents of the S-beta-hydroxybutyrate enantiomer and 43% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-3. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 5

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 60% by enantiomeric equivalents of the S-beta-hydroxybutyrate enantiomer and 40% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-4. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 6

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 65% by enantiomeric equivalents of the S-beta-hydroxybutyrate enantiomer and 35% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-5. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 7

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 70% by enantiomeric equivalents of the S-beta-hydroxybutyrate enantiomer and 30% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-6. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 8

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 75% by enantiomeric equivalents of the S-beta-hydroxybutyrate enantiomer and 25% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-7. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 9

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 85% by enantiomeric equivalents of the S-beta-hydroxybutyrate enantiomer and 15% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-6. On the other hand, including the S-betahydroxybutyrate enantiomer provides for a longer state of ketosis and/or other benefits as disclosed herein, as compared to a composition enriched with the R-beta-hydroxybutyrate enantiomer.

Example 10

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide from 90%, 91%, 92%, 93%, 94%, 95%, 96%, 97%, 98%, or 99% by enantiomeric equivalents of the S-beta-hydroxybutyrate enantiomer and 10%, 9%, 8%, 7%, 6%, 5%, 4%, 3%, 2%, or 1% by enantiomeric equivalents of the R-beta-hydroxybutyrate enantiomer. Because the non-racemic mixture includes substantially less of the R-beta-hydroxybutyrate enantiomer, the onset of ketosis is significantly delayed for a given dosage as compared to the same dosage of racemic mixture or the non-racemic mixtures of Examples 1-9. On the other hand, including the S-beta-hydroxybutyrate enantiomer provides for a longer state of ketosis and/or other benefits as disclosed herein.

Example 11

A composition comprising one or more S-beta-hydroxybutyrate compounds is mixed with a carrier to form a composition with 100% equivalents of S-beta-hydroxybutyrate enantiomer and 0% equivalents of R-beta-hydroxybutyrate enantiomer. Because the composition contains no R-beta-hydroxybutyrate enantiomer, the onset of ketosis is significantly delayed for a given dosage as compared to the same dosage of racemic mixture or the non-racemic mixtures of Examples 1-10. On the other hand, including the S-beta-hydroxybutyrate enantiomer provides for a delayed and/or longer state of ketosis and/or other benefits as disclosed herein.

Example 12

Any of the foregoing examples is modified by combining the non-racemic mixture of S-beta-hydroxybutyrate and R-beta-hydroxybutyrate with a dietetically or pharmaceutically acceptable carrier.

Example 13

Any of the foregoing examples is modified by combining the non-racemic mixture of S-beta-hydroxybutyrate and R-beta-hydroxybutyrate with one or more medium chain triglycerides and/or one or more medium chain fatty acids and/or one or more mono- or diglycerides medium chain fatty acids.

Example 14

Any of the foregoing examples is modified by combining the non-racemic mixture of S-beta-hydroxybutyrate and R-beta-hydroxybutyrate with one or more supplements, such as vitamin $D_3$, vitamins, minerals, and others known in the art.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of administering a ketone body composition to a subject, the ketone body composition comprising:
   a non-racemic mixture of S-beta-hydroxybutyrate and R-beta-hydroxybutyrate that is enriched with the S-beta-hydroxybutyrate relative to the R-beta-hydroxybutyrate,
   wherein the non-racemic mixture comprises less than 100% by enantiomeric equivalents of the S-beta-hydroxybutyrate and greater than 0% by enantiomeric equivalents of the R-beta-hydroxybutyrate.

2. The method of claim 1, wherein the non-racemic mixture contains from 52% to 99% by enantiomeric equivalents of the S-beta-hydroxybutyrate and 48% to 1% by enantiomeric equivalents of the R-beta-hydroxybutyrate.

3. The method of claim 1, wherein the non-racemic mixture contains from 53% to 99% by enantiomeric equivalents of the S-beta-hydroxybutyrate and 47% to 1% by enantiomeric equivalents of the R-beta-hydroxybutyrate.

4. The method of claim 1, wherein the non-racemic mixture contains from 55% to 98% by enantiomeric equivalents of the S-beta-hydroxybutyrate and 45% to 2% by enantiomeric equivalents of the R-beta-hydroxybutyrate.

5. The method of claim 1, wherein the non-racemic mixture contains from 57% to 96% by enantiomeric equivalents of the S-beta-hydroxybutyrate and 43% to 4% by enantiomeric equivalents of the R-beta-hydroxybutyrate.

6. The method of claim 1, wherein the non-racemic mixture contains from 60% to 96% by enantiomeric equivalents of the S-beta-hydroxybutyrate and 40% to 4% by enantiomeric equivalents of the R-beta-hydroxybutyrate.

7. The method of claim 1, wherein the composition comprises one or more salts of S-beta-hydroxybutyrate.

8. The method of claim 7, wherein the one or more salts of S-beta-hydroxybutyrate comprise at least one of a sodium salt, potassium salt, magnesium salt, calcium salt, transition metal salt, or amino acid salt of S-beta-hydroxybutyrate.

9. The method of claim 1, wherein the non-racemic mixture contains at least one S-beta-hydroxybutyrate ester.

10. The method of claim 9, wherein the S-beta-hydroxybutyrate ester is a di-ester of a diol and S-beta-hydroxybutyrate.

11. The method of claim 9, wherein the S-beta-hydroxybutyrate ester comprises at least one of mono-ester of ethanol, mono-ester of 1-propanol, mono-ester of 1,3-propanediol, di-ester of 1,3-propanediol, mono- or di-ester of S-1,3-butanediol, mono- or di-ester of R-1,3-butanediol, mono- or di-ester of S-R-1,3-butanediol, or mono-, di-, or tri-ester of glycerin.

12. The method of claim 1, wherein the composition further comprises a carrier, and wherein the carrier comprises a powder, a liquid, a tablet, a capsule, a food product, a food additive, a beverage, a beverage additive, a food supplement a spray, a suppository, a pastille, a sucker, or a candy.

13. The method of claim 1, further comprising vitamin $D_3$.

14. The method of claim 1, wherein the composition further comprises at least one medium chain fatty acid having from 6 to 12 carbons, or a mono-, di- or triglyceride of the at least one medium chain fatty acid.

15. The method of claim 14, wherein the at least one medium chain fatty acid has from 8 to 10 carbons.

16. The method of claim 1, wherein the composition further comprises at least one of (i) a short chain fatty acid, or a mono-, di- or triglyceride of the at least one short chain fatty acid, having fewer than 6 carbons or (ii) a long chain fatty acid, or a mono-, di- or triglyceride of the at least one long chain fatty acid, having more than 12 carbons.

17. The method of claim 1, wherein administration of the composition results in one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, or improved body composition.

18. The method of claim 1, wherein administration of the composition results in at least one of:
    increased endogenous production of R-beta-hydroxybutyrate and acetoacetate;
    endogenous conversion of the S-beta-hydroxybutyrate into one or both of R-beta-hydroxybutyrate and acetoacetate;
    endogenous conversion of the S-beta-hydroxybutyrate into fatty acids and sterols;
    prolonged ketosis;
    metabolism of the S-beta-hydroxybutyrate independent of conversion to R-beta-hydroxybutyrate and/or acetoacetate;
    increased fetal development;
    increased growth years;
    reduced endogenous production of acetone during ketosis;
    signaling by the S-beta-hydroxybutyrate that modulates metabolism of R-beta-hydroxybutyrate and glucose;
    antioxidant activity;
    production of acetyl-CoA.

19. A method of administering a nutritionally or pharmaceutically effective amount of a ketone body composition to a subject, the composition comprising:
    S-beta-hydroxybutyrate ester or a non-racemic mixture of the S-beta-hydroxybutyrate ester and R-beta-hydroxybutyrate, wherein the composition comprises from 52% to 100% by enantiomeric equivalents of the S-beta-hydroxybutyrate ester and 48% to 0% by enantiomeric equivalents of the R-beta-hydroxybutyrate.

20. A method of administering a nutritionally or pharmaceutically effective amount of a ketone body composition to a subject, the composition comprising:
    a nutritionally or pharmaceutically acceptable carrier; and
    a non-racemic mixture of S-beta-hydroxybutyrate and R-beta-hydroxybutyrate that is enriched with the S-beta-hydroxybutyrate relative to the R-beta-hydroxybutyrate, wherein the composition comprises less than 100% by enantiomeric equivalents of the S-beta-hydroxybutyrate and greater than 0% by enantiomeric equivalents of the R-beta-hydroxybutyrate.

* * * * *

UNITED STATES PATENT AND TRADEMARK OFFICE
CERTIFICATE OF CORRECTION

PATENT NO. : 10,596,128 B2
APPLICATION NO. : 16/224485
DATED : March 24, 2020
INVENTOR(S) : Gary Millet It is certified that error appears in the above-identified patent and that said Letters Patent is hereby corrected as shown below:

On the Title Page

Page 2

Item (56), Reference Cited, change "Henderson, Samuel T. "Ketone bodies as a Therapeutic for Alzheimer's Disease." Neurotherapeutics. Jul. 2008; 5 3 3): 470-80" to – Henderson, Samuel T. "Ketone bodies as a Therapeutic for Alzheimer's Disease." Neurotherapeutics. Jul. 2008; 5(3): 470-80." –

Item (56), References Cited, change "Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essent Fatty Acids. Mar 2004; 70 (3): 309-19." to – Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essential Fatty Acids. Mar 2004; 70 (3): 309-19. –

Item (56), References Cited, change "Krotkiewski, M. "Value of VLCD Supplementation with Medium Chain Triglycerides." I'nt JobesRelatMetab Disord. Sep. 2001; 25(9):1 393/\00." to – Krotkiewski, M. "Value of VLCD Supplementation with Medium Chain Triglycerides." International Journal of Obesity and Related Metabolic Disorders. Sep. 2001; 25(9):1393-1400 –

In the Specification

Column 2
Line 9, change "to entering" to – for entering –

Column 8
Line 22, change "includes" to – include –

Signed and Sealed this
Twenty-eighth Day of July, 2020

Andrei Iancu
*Director of the United States Patent and Trademark Office*

Column 13
Line 53, change "diglycerides" to – diglycerides of –